United States Patent [19]

Briner

[11] Patent Number: 5,075,513
[45] Date of Patent: Dec. 24, 1991

[54] CYCLOPENTANE DERIVATIVES

[75] Inventor: Paul H. Briner, Canterbury, England

[73] Assignee: Shell Internationale Research Maatschappij B.V., Netherlands

[21] Appl. No.: 397,720

[22] Filed: Aug. 23, 1989

[30] Foreign Application Priority Data

Aug. 31, 1988 [GB] United Kingdom ................ 8820604
Aug. 31, 1988 [GB] United Kingdom ................ 8820605
Aug. 31, 1988 [GB] United Kingdom ................ 8820606

[51] Int. Cl.$^5$ ............................................. C07C 31/18
[52] U.S. Cl. .................................. 568/852; 568/814; 570/183
[58] Field of Search ................ 568/852, 814; 570/183

[56] References Cited

FOREIGN PATENT DOCUMENTS 267778  5/1988  European Pat. Off. ............ 548/262
3630840 3/1987  Fed. Rep. of Germany ...... 548/262

Primary Examiner—Jose G. Dees
Assistant Examiner—D. D. Carr

[57] ABSTRACT

The invention provides cyclopentane derivatives of the general formula

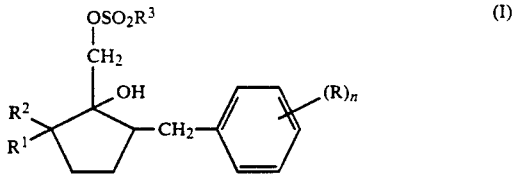

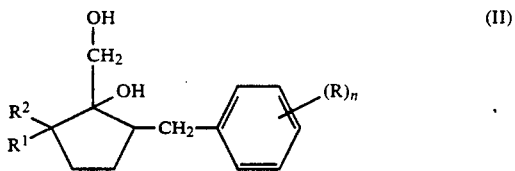

and

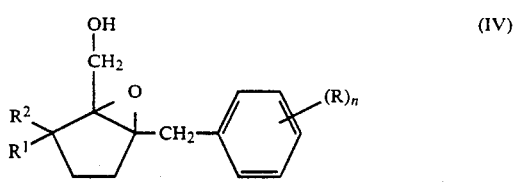

in which n represents an integer from 0 to 5, each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkythio, alkysulphinyl, alkylsulphonyl, carbamoyl, alkylamindo, cycloalkyl or phenyl group, $R^1$ and $R^2$ independently represent a hydrogen atom or an alkyl group, and $R^3$ represents an optionally substituted alkyl or aryl group; and a process for their preparation. Compounds of formulae I, II and IV are useful as intermediates in the preparation of certain fungicidally active cyclopentane derivatives. Also, certain compounds of formula IV are themselves fungicidally active.

3 Claims, No Drawings

CYCLOPENTANE DERIVATIVES

This invention relates to certain cyclopentane derivatives, which are useful as intermediates in the preparation of fungicidally active cyclopentane derivatives, and a process for their preparation. Certain cyclopentane derivatives according to the present invention are themselves fungicidally active and the invention therefore also relates to compositions containing such compounds and their use as fungicides.

According to the present invention there is provided a compound of the general formula

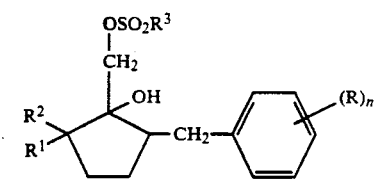

(I)

in which n represents an integer from 0 to 5; each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group; $R^1$ and $R^2$ independently represent a hydrogen atom or an alkyl group; and $R^3$ represents an optionally substituted alkyl or aryl group.

Also according to the present invention there is provided a compound of the general formula

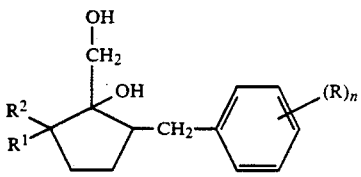

(II)

in which n, R, $R^1$ and $R^2$ are as defined above.

Further according to the present invention there is provided a compound of the general formula

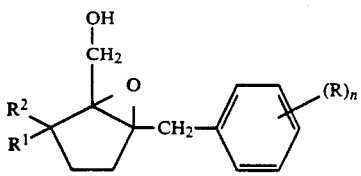

(I)

in which n, R, $R^1$ and $R^2$ are as defined above.

When any of the foregoing substituents represents or contains an alkyl substituent group, this may be linear or branched and may contain up to 12, preferably up to 6, and especially up to 4, carbon atoms. A cycloalkyl substituent group may contain 3 to 8, preferably 3 to 6, carbon atoms.

It is preferred that $R^3$ represents a $C_{1-4}$alkyl group or a phenyl group each optionally substituted by one or more substituents selected from halogen atoms, nitro, cyano, hydroxyl, $C_{1-4}$alkyl, $C_{1-4}$haloalkyl, $C_{1-4}$alkoxy, $C_{1-4}$haloalkoxy, amino, $C_{1-4}$alkylamino, di-$C_{1-4}$alkylamino, $C_{1-4}$alkoxycarbonyl, carboxyl, $C_{1-4}$alkanoyl, $C_{1-4}$alkylthio, $C_{1-4}$alkylsulphinyl, $C_{1-4}$alkylsulphonyl, carbamoyl, $C_{1-4}$alkylamido, $C_{3-8}$cycloalkyl and phenyl groups. Most preferably, $R^3$ represents a methyl or toluene group.

It is preferred that $R^1$ and $R^2$ independently represent a hydrogen atom or a $C_{1-4}$alkyl, particularly a methyl, group.

Preferably, R represents a halogen, especially a chlorine, atom.

A particularly preferred sub-group of compounds of formulae I, II and IV is that in which n is 1, R represents a chlorine atom, preferably substituted at the 4-position of the phenyl ring, and $R^1$ and $R^2$ both represent a hydrogen atom or both represent a methyl group.

The compounds of formulae I and II exist in two stereoisomeric forms which have the following structures:

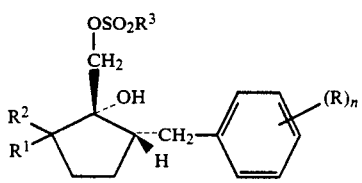

(IA)

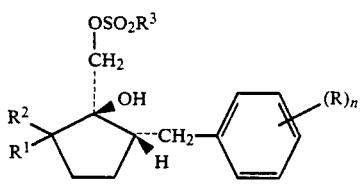

(IB)

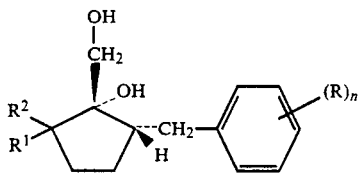

(IIA)

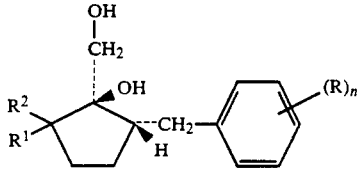

(IIB)

The letters A and B will be used hereinafter to denote compounds having the same stereochemical configuration as isomers IA and IB above. Isomers IA and IB and isomers IIa and IIb can be separated by, for instance, chromatography.

The present invention also provides a process for the preparation of a compound of formula I as defined above which comprises reacting a compound of the general formula

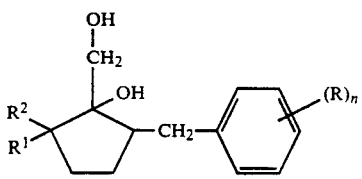

(II)

in which n, R, $R^1$ and $R^2$ are as defined above, with a compound of the general formula

R³SO₂S (III)

in which R³ is as defined above and X represents a halogen, preferably a chlorine or bromine, atom in the presence of a base.

It is preferred that the base is an organic base and, in particular, a tertiary base. Suitable bases include triethylamine, tributylamine and pyridine.

The process may be carried out in the presence of a solvent. Suitable solvents include hydrocarbons, such as toluene, and chlorinated hydrocarbons, such as dichloromethane.

The reaction is suitably carried out at a low temperature, the preferred temperature being from −20° C. to room temperature. A particularly preferred temperature range is from −10° C. to 20° C.

Compounds of formula IA may be synthesised from compounds of formula IIA and compounds of formula IB may be synthesised from compounds of formula IIB by the above process.

The present invention further provides a process for the preparation of a compound of formula IIA as defined above which comprises either reacting a compound of the general formula

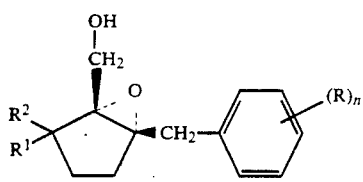

(IV)

in which n, R, R¹ and R² are as defined above, with a reducing agent at a temperature from 35° C. to reflux temperature; or reacting a compound of the general formula

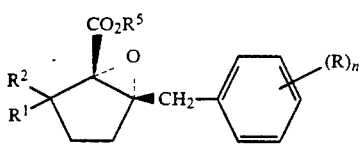

(V)

in which n, R, R¹ and R² are as defined above and R⁵ represents a hydrogen atom or an alkyl, preferably C₁₋₆alkyl, or cycloalkyl group, with a reducing agent at a temperature from 35° C. to reflux temperature.

The reducing agent is preferably a complex metal hydride such as lithium aluminium hydride or sodium aluminium hydride, lithium aluminium hydride being especially preferred.

The process is conveniently carried out in the presence of a solvent. Suitable solvents include lower ethers such as diethyl ether, tetrahydrofuran and higher ethers, such as glymes, for instance, 1,2-dimethoxyethane.

It is advisable to destroy any excess reducing agent remaining at the end of the reduction process to prevent further reaction. If a complex metal hydride, such as lithium aluminium hydride, is used as reducing agent, any excess may be destroyed by the addition of water and sodium hydroxide or ammonium chloride to the reaction mixture.

A feature of the above reactions is that they are stereospecific. This is due to the presence of the epoxy group in the starting materials of formula IV and formula V. It has been found that the regioselectivity of these reactions may be improved further by the addition of a Lewis acid, such as aluminium chloride.

The present invention still further provides a process for the preparation of a compound of formula IV as defined above which comprises reacting a compound of formula V, as defined above, with a reducing agent.

The reducing agent is preferably a complex metal hydride, such as lithium aluminium hydride, sodium aluminium hydride, "REDAL" (Trade Mark: sodium bis(2-methoxyethoxy)aluminiumhydride in toluene) or sodium borohydride, optionally in the presence of a Lewis acid, such as aluminium chloride.

Preferably, the reaction is carried out at a temperature from room temperature to 85° C., depending on the nature of the reducing agent selected.

The process is conveniently carried out in the presence of a solvent. Suitable solvents include ethers such as diethyl ether, tetrahydrofuran and glymes, and hydrocarbons such as toluene.

Again, it is advisable to destroy any excess reducing agent remaining at the end of the reduction process to prevent further reaction. If a complex metal hydride, such as lithium aluminium hydride, is used as reducing agent, any excess may be destroyed by the addition of water and sodium hydroxide to the reaction mixture.

Compounds of formula V may be conveniently prepared by reacting a compound of the general formula

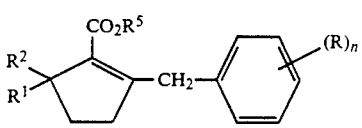

(VI)

in which n, R, R¹, R² and R⁵ are as defined above, with a peracid, such as peracetic acid, perbenzoic acid or perphthalic acid. The compounds of formula V and a process for their preparation form the subject of copending patent application T 622a.

Compounds of formula VI may be conveniently prepared by heating a compound of the general formula

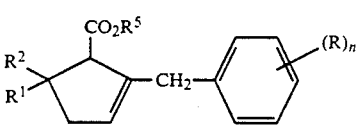

(VII)

or the general formula

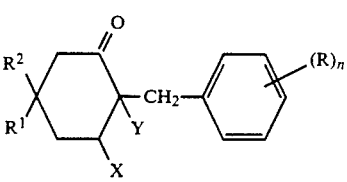

(VIII)

in which n, R, R¹, R² and R⁵ are as defined above and X and Y independently represent a halogen, preferably a chlorine or bromine, atom, with a compound of the general formula

MOR⁵ (IX)

in which R⁵ is as defined above and M represents an alkali metal, preferably a sodium, atom, in the presence of a polar solvent. It is preferred that the polar solvent is a compound of the general formula $$R^5OH \quad (X)$$

in which $R^5$ is as defined above. Preferably, $R^5$ has the same meaning in formula IX and formula X. For instance, if the compound of formula IX is sodium methoxide, it is preferred that the solvent of formula X is methanol. The compounds of formula VI and a process for their preparation form the subject of copending patent application T 616.

Compounds of formula VII may be conveniently prepared by reacting a compound of formula VIII, as defined above, with a compound of formula IX, as defined above, in the presence of a solvent X, as defined above, preferably at a temperature in the range of 0°-20° C. The compounds of formula VII and a process for their preparation form the subject of copending patent application T 616.

Compounds of formula VIII may be conveniently prepared by reacting a compound of the general formula

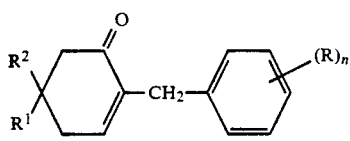

in which n, R, $R^1$ and $R^2$ are as defined above, with a compound XY, in which X and Y are as defined above. Alternatively, compounds of formula VIII may be generated in situ and then heated with a compound of formula IX in the presence of a solvent of formula X as described above to form compounds of formula VI in a one-pot synthesis. The compounds of formula VIII and a process for their preparation form the subject of copending patent application T 616.

Compounds of formula XI may be conveniently prepared by reacting a compound of the general formula

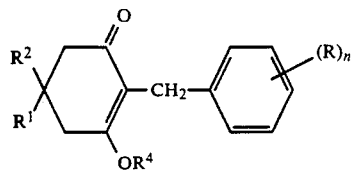

in which n, R, $R^1$ and $R^2$ are as defined above and $R^4$ represents an alkyl, preferably a $C_{1-4}$alkyl, group, with a suitable reducing agent, for instance, a complex metal hydride, such as lithium aluminium hydride or sodium aluminium hydride, or hydrogen in combination with a catalyst, and subsequently hydrolysing the reaction mixture. The compounds of formula XI and a process for their preparation form the subject of copending patent application T 616.

Compounds of formula XII may be conveniently prepared by reacting a compound of the general formula

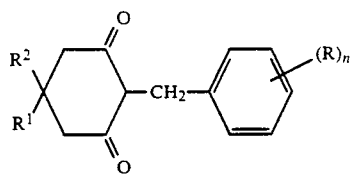

in which n, R, $R^1$ and $R^2$ are as defined above, with a compound of the general formula $$R^4OH \quad (XIV)$$

in which $R^4$ is as defined above, in the presence of an acid, such as sulphuric acid, p-toluenesulphonic acid or an ion exchange resin. The compounds of formula XII and a process for their preparation form the subject of copending patent application T 616.

Compounds of formula XIII may be conveniently prepared by reacting a compound of the general formula

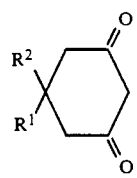

in which $R^1$ and $R^2$ are as defined above, with a compound of the general formula

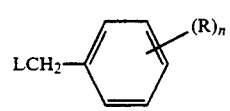

in which R and n are as defined above and L represents a suitable leaving group, in the presence of a suitable base, such as potassium hydroxide.

Compounds of formula III, IX, X, XIV, XV and XVI and the compounds XY are known compounds or can be prepared by processes analogous to known processes.

In another aspect, the present invention provides a process for the preparation of a compound of formula IIB as defined above which comprises reacting a compound of the general formula

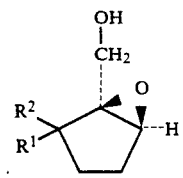

in which $R^1$ and $R^2$ are as defined above, with a compound of the general formula

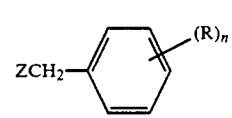

in which n and R are as defined above and Z represents a lithium atom or a group —MgX where X represents a halogen, preferably a bromine atom. This reaction is stereospecific due to the presence of the epoxy group in the starting material of formula XVII.

Compounds of formula XVII may be conveniently prepared by reacting a compound of the general formula

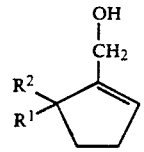 (XIX)

in which $R^1$ and $R^2$ are as defined above, with a peracid, such as peracetic acid, perbenzoic acid or perphthalic acid.

Compounds of formula XIX may be conveniently prepared by reacting a compound of the general formula

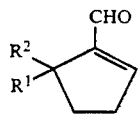 (XX)

in which $R^1$ and $R^2$ are as defined above, with a suitable reducing agent, for instance, a complex metal hydride, such as lithium aluminium hydride, sodium aluminium hydride, sodium borohydride or "REDAL" (Trade Mark: sodium bis(2-methoxyethoxy)aluminiumhydride in toluene).

Compounds of formula XVIII and XX are known compounds or can be prepared by processes analogous to known processes.

The compounds of formulae I, II and IV are useful as intermediates in the preparation of fungicidally active cyclopentane derivatives of the general formula

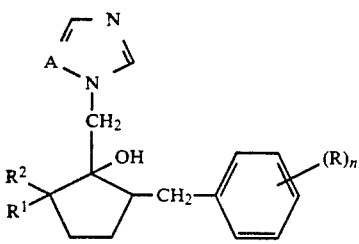 (XXI)

in which n, R, $R^1$ and $R^2$ are as defined above and A represents a nitrogen atom or a CH group. Certain compounds of formula XXI are the subject of co-pending patent applications GB-A1-2180236 and EP-A2-0267778.

The compounds disclosed in EP-A2-0267778 and GB-A1-2180236 exist in two stereoisomeric forms which have the following structures:

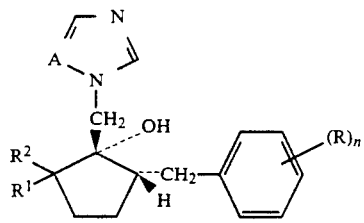 (XXIA)

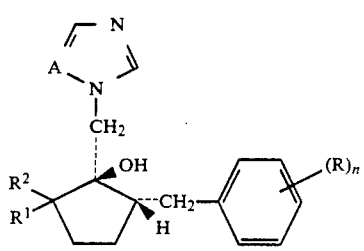 (XXIB)

Isomers A and B can be separated by, for instance, chromatography and exhibit different fungicidal activity. Generally, isomers of formula XXIA exhibit greater fungicidal activity than isomers of formula XXIB. The process used to synthesise compounds of formula XXIA from compounds of formula I, II and IV is set out in the following reaction scheme:

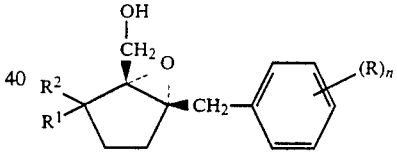

(IV)

Reduction
(e.g. LiAlH4) ↓

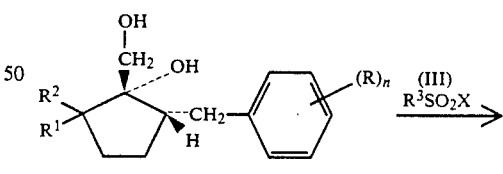

(IIA)

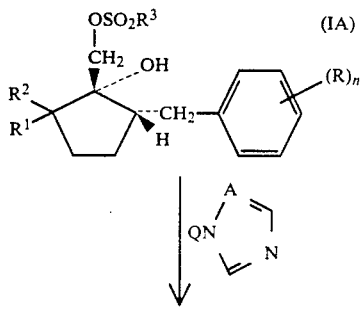

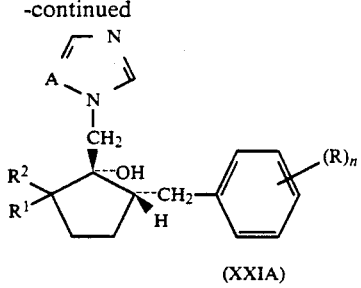

(XXIA)

Compounds of formula XXIB can be synthesised from compounds of formula IIB by an exactly analogous process.

In the above reaction scheme, n, R, $R^1$, $R^2$, $R^3$ and A are as previously defined and Q represents a hydrogen or, alkali metal, preferably sodium, atom. The process step in the above reaction scheme is the subject of copending patent application T 626.

Certain compounds of formula IV have also been found to have fungicidal activity. Accordingly, the invention further provides a fungicidal composition which comprises a carrier and, as active ingredient, a compound of formula IV as defined above. A method of making such a composition is also provided which comprises bringing a compound of formula IV into association with at least one carrier. Such a composition may contain a single compound or a mixture of several compounds of formula IV.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium ,silicates; elements, for example carbon and sulphur; natural and synthetic resins, for example coumarone resins, polyvinyl chloride, and styrene polymers and copolymers: solid polychlorophenols: bitumen: waxes, for example beeswax, paraffin wax, and chlorinated mineral waxes: and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example, kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ½-10% w of active ingredient. Granules are usually prepared to have a size between 10 and 100 BS mesh (1.676-0.152 mm), and may be manufactured by agglomeration or impregnation techniques. Generally, granules will contain ½-75% w active ingredient and 0-10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1-50% w/v active ingredient, 2-20% w/v emulsifiers and 0-20% w/v of other additives such as stabilisers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agent such as protective colloids and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a plant, or could include an adhesive component enabling them to be applied directly to the stem of a plant.

The invention still further provides the use as a fungicide of a compound of the general formula IV as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The invention is further illustrated by the following Examples.

EXAMPLE 1

Preparation of 1-(4-chlorobenzyl)-1,2-epoxy-3,3-dimethyl-2-hydroxymethylcyclopentane (Formula IV: n=1, R=4-Cl, $R^1=R^2=CH_3$)

(a) Preparation of 2-(4-chlorobenzyl)-5,5-dimethylcyclohexane-1,3-dione 449 g (3.21 mols) dimedone (5,5-dimethylcyclohexane-1,3-dione) were added to a solution of aqueous potassium hydroxide comprising 166 g of 85% potassium hydroxide (2.52 moles) in 700 ml of water. The mixture was then warmed and a clear orange solution was obtained at 47° C. The solution was then heated to 59° C. and 544 g (3.21 mols) molten 4-chlorobenzyl chloride were added over a period of 1 hour with further heating to 85° C. Heating was continued for a further 2¼ to 3 hours up to a temperature of 100° C. The mixture was then cooled, the solid product filtered off, washed with water and dried in a vacuum oven at 50° C. The crude solid (815 g) was then dissolved in 2400 ml methanol at reflux and 200 ml water added to produce a permanent cloudiness. The mixture was then allowed to cool to room temperature overnight with stirring. The solid so obtained was filtered, washed with about 400 ml cold methanol and dried in a vacuum oven to produce 340 g 2-(4-chlorobenzyl)-5,5-dimethylcyclohexane-1,3-dione as a white solid, m.pt. 188°–190° C. Yield: 42%.

(b) Preparation of 2-(4-chlorobenzyl)-3-(2-methylpropoxy)-5,5-dimethylcyclohex-2-en-1-one 325 g (1.23 mol) of the 2-(4-chlorobenzyl)-5,5-dimethylcyclohexane-1,3-dione obtained in (a), 1.6 liters toluene, 182 g (2.5 mol) isobutanol and 5 g p-toluenesulphonic acid were stirred together at reflux under a Dean-Stark apparatus. The temperature of the reaction mixture was approximately 90° C. As water distilled off, the reaction mixture changed from a thin slurry to a yellow solution. After 14 hours reflux, the reaction mixture was cooled and shaken twice with 500 ml aliquots of 10% aqueous sodium hydroxide. The toluene layer was then flashed to give 389 g yellow/orange oil which crystallised on standing. Recrystallisation of the solid from 60/80 petroleum produced 331 g 2-(4-chlorobenzyl)-3-(2-methylpropoxy)-5,5-dimethylcyclohex-2-en-1-one as a white crystalline solid, m.pt. 60°–61° C. Yield: 84%.

(c) Preparation of 2-(4-chlorobenzyl)-3-methoxy-5,5-dimethylcyclohex-2-en-1-one

A solution of 154 g of the 2-(4-chlorobenzyl)-3-(2-methylpropoxy)-5,5-dimethylcyclohex-2-en-1-one obtained in Example 1 in 1200 ml methanol containing 3 g p-toluenesulphonic acid was refluxed for 2 hours. The reaction mixture was then extracted with 3 liters water and 1 liter diethyl ether and re-extracted with a further 1 liter diethyl ether. The organic phases were then back-washed first with 200 ml 10% aqueous sodium hydroxide and then with 100 ml saturated sodium chloride solution, dried over anhydrous magnesium sulphate and flashed. The residue was then crystallised in 60/80 petroleum, filtered and air-dried to give 98 g 2-(4-chlorobenzyl)-3-methoxy-5,5-dimethylcyclohex-2-en-1-one as a white solid, m.pt. 62°–63° C. Yield: 73%.

(d) Preparation of 2-i4-chlorobenzyl)-5,5-dimethylcyclohex-2-en-1-one 98 g (0.35 mol) of the 2-(4-chlorobenzyl)-3-methoxy-5,5-dimethylcyclohex-2-en-1-one obtained in (c) were added to a slurry of 6.65 g (0.175 mol) lithium aluminium hydride in 490 mls diethyl ether at a rate sufficient to maintain reflux and the final reaction mixture refluxed for a further 30 minutes. 5 ml water were then added, followed by 5 ml 15% aqueous sodium hydroxide and a further 15 ml water and the resulting precipitate was filtered off. The filtrate was then shaken in 200 ml 5M hydrochloric acid for five minutes and the organic layer then separated, washed twice with 100 ml aliquots of saturated sodium bicarbonate solution, dried over anhydrous magnesium sulphate and stripped. The resulting oil was then dissolved in 430 mls dichloromethane, 18 g (0.085 mols) pyridinium chlorochromate were added and the reaction mixture stirred for 3 hours. 600 ml diethyl ether were added and the solid was then filtered off. The filtrate was washed three times with 10% sodium hydroxide, once with 2.5M hydrochloric acid and once with saturated sodium bicarbonate solution. It was then dried over anhydrous magnesium sulphate and stripped to give 82 g of crude product. Distillation of the crude product under reduced pressure (0.15 mm mercury) gave 79 g 2-(4-chlorobenzyl)-5,5-dimethylcyclohex-2-en-1-one, b.pt. 130° C. at 0.15 mm mercury. Yield: 91%.

(e) Preparation of 2-(4-chlorobenzyl)-2,3-dibromo-5,5-dimethylcyclohexan-1-one 10 g (40.2 mmol) of the 2-(4-chlorobenzyl)-5,5-dimethylcyclohex-2-en-1-one obtained in (d) were dissolved in 50 ml 30/40 petroleum at 0° C. 6.72 g (40.2 mmol) bromine were then added to the solution. After 5–10 minutes, the solution decolourised and a precipitate formed. The solution was then cooled further and the precipitate filtered off to give 12.4 g 2-(4-chlorobenzyl)-2,3-dibromo-5,5-dimethylcyclohexan-1-one as a solid, m.pt. 82°–84° C. Yield 75%.

(f) Preparation of 1-(4-chlorobenzyl)-3,3-dimethyl-2-methoxycarbonylcyclopent-1-ene A solution of sodium methoxide was prepared by adding 2.8 g (121 mmol) sodium to 50 ml methanol. A slurry of the 2-(4-chlorobenzyl)-2,3-dibromo-5,5-dimethylcyclohexan-1-one obtained in (e) in methanol was then prepared and added to the sodium methoxide solution at reflux. Reflux was continued overnight. The reaction mixture was then quenched with 200 ml water, extracted twice with 100 ml aliquots of diethyl ether, backwashed with water, dried over anhydrous magnesium sulphate and flashed to give 8 g of a yellow oil. By gas chromatography analysis, it was established that 6.6 g 1-(4-chlorobenzyl)-3,3-dimethyl-2-methoxycarbonylcyclopent-1-ene were produced as an oil. The structure of the product was established by n.m.r. spectroscopy. Yield: 78%.

(g) Preparation of 1-(4-chlorobenzyl)-1,2-epoxy-3,3-dimethyl-2-methoxycarbonylcyclopentane 23.5 g (3 equivalents) "PROXITANE 4002" (Trade Mark: 36–40% (w/w) peracetic acid in acetic acid) were added to 9.8 g (35.1 mmol) 1-(4-chlorobenzyl)-3,3-dimethyl-2-methoxycarbonylcyclopent-1-ene prepared as described in (f) in 90 ml trichloromethane. The resulting mixture was refluxed for 3 hours, diluted with water and then the aqueous phase was re-extracted twice with 50 ml aliquots of trichloromethane, and the combined extracts backwashed once with 50 ml dilute sodium bicarbonate solution and twice with 50 ml aliquots of saturated sodium metabisulphite, washed with saturated sodium chloride solution, dried over anhydrous magnesium sulphate and flashed to give 12 g of a pale yellow oil which crystallised on cooling. Trituration in 30/40 petroleum gave 5.8 g 1-(4-chlorobenzyl)-1,2-epoxy-3,3-dimethyl-2-methoxycarbonylcyclopentane as a white crystalline solid, m.pt. 86°-87° C. Yield: 56%.

(h) Preparation of 1-(4-chlorobenzyl)-1,2-epoxy-3,3-dimethyl-2-hydroxymethylcyclopentane 10.7 g (36.3 mmol) 1-(4-chlorobenzyl)-1,2-epoxy-3,3-dimethyl-2-methoxycarbonylcyclopentane prepared as described in (g) were dissolved in diethyl ether and the resulting solution was then added to a slurry of 1.5 g (36.6 mmol) lithium aluminium hydride in 50 ml diethyl ether at a rate such that reflux of the reaction mixture was maintained. Heating was continued for 5 minutes after the last addition of 1-(4-chlorobenzyl)-1,2-epoxy-3,3-dimethyl-2-methoxycarbonylcyclopentane solution. 1.25 ml water were then added, followed by 1.25 ml 15% aqueous sodium hydroxide solution and a further 4 ml water. The solid was filtered off and the filtrate was then dried over anhydrous magnesium sulphate and flashed to give a clear oil which crystallised on cooling to give 9.6 g 1-(4-chlorobenzyl)-1,2-epoxy-3,3-dimethyl-2-hydroxymethylcyclopentane as a solid, m.pt. 36°-38° C.

EXAMPLE 2

Preparation of
1-(4-chlorobenzyl)-3,3-dimethyl-2-hydroxy-2-hydroxymethylcyclopentane (Isomer A)

(Formula IIA: n=1, R=4-Cl, $R^1$=$R^2$=$CH_3$)

2.7 g (71 mmol) lithium aluminium hydride were added to a suspension of 2.7 g (24 mmol) aluminium chloride partially dissolved in 120 ml 1,2-dimethoxyethane, the addition of lithium aluminium hydride causing a rise in temperature to 50° C. The resulting slurry was incubated at 50° C. for 30 minutes. A solution of 6.8 g (23 mmol) 1-(4-chlorobenzyl)-1,2-epoxy-3,3-dimethyl-2-methoxycarbonylcyclopentane prepared as described in Example 1 (g) in 30 ml 1,2-dimethoxyethane was then added over a period of 30 minutes whilst maintaining the temperature of the reaction mixture at 50°-55° C. After 1 hour, thin layer chromatography indicated that the reaction was complete and the excess lithium aluminium hydride was therefore destroyed by adding 10 ml saturated ammonium chloride solution followed by 10 ml water. This produced a sludgy solid which filtered only slowly. After filtration, the solid was dissolved in 2N hydrochloric acid and extracted twice with diethyl ether. The extracts were combined with the filtrate and flashed to give 5.9 g crude product. Trituration with cold 60/80 petroleum and a little diethyl ether gave 5.45 g 1-(4-chlorobenzyl)-3,3-dimethyl-2-hydroxy-2-hydroxymethylcyclopentane as a white solid, m.pt. 103°-104° C. Yield: 82%.

EXAMPLE 3

Preparation of
1-(4-chlorobenzyl)-3,3-dimethyl-2-hydroxy-2-methylsulphonyloxymethylcyclopentane (Isomer A)

(Formula IA: n=1, R=4-Cl, $R^1$=R=$CH_3$, $R^3$=$CH_3$)

2.76 g (1.05 equivalents) methylsulphonyl chloride were added to a solution of 6.42 g (24 mmol) 1-(4-chlorobenzyl)-3,3-dimethyl-2-hydroxy-2-hydroxymethylcyclopentane prepared as described in Example 2 and 2.55 g (1.1 equivalents) triethylamine in 50 ml dichloromethane at 10°-15° C. The reaction mixture was kept at 10°-15° C. for a further 2 hours and then washed with 20 ml water, then 20 ml aqueous sodium bicarbonate solution, dried over anhydrous magnesium sulphate and flashed. Trituration with 60/80 petroleum gave 6.64 g 1-(4-chlorobenzyl)-3,3-dimethyl-2-hydroxy-2-methylsulphonyloxymethylcyclopentane as a white solid, m.pt. 113°-114° C. Yield: 80%.

EXAMPLE 4

The fungicidal activity of the compound of Example 1 was investigated by means of the following test.

Activity against Fusarium in-vitro (Fusarium species; FsI)

This test measures the in vitro activity of compounds against a species of Fusarium that causes stem and root rots.

Compound is dissolved or suspended in acetone and added to molten half strength Potato Dextrose Agar to give a final concentration of 100 ppm compound and 3.5% acetone. After the agar has set, plates are inoculated with 6 mm diameter plugs of agar and mycelium taken from a 7 day old culture of Fusarium sp.

Plates are incubated at 20° C. for 5 days and radial growth from the plug is measured.

The extent of disease control in the above test is expressed as a rating compared with either an untreated control or a diluent-sprayed-control, according to the criteria:

0 = less than 50% disease control
1 = about 50-80% disease control
2 = greater than 80% disease control The result of this test is set out in the Table below:

| Compound Example No. | Fungicidal Activity FsI |
|---|---|
| 1 | 1 |

I claim:
1. A compound of the formula:

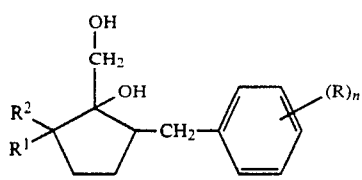

in which
   n represents an integer from 0 to 5;
   each R represents a halogen atom, nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group; and
   $R^1$ and $R^2$ independently represent a hydrogen atom or an alkyl group.

2. A process for the preparation of a compound of formula

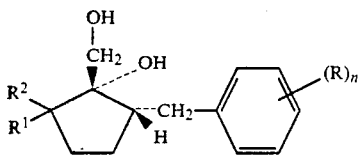 (IIA)

according to claim 1 which comprises either
   (a) reacting a compound of the general formula

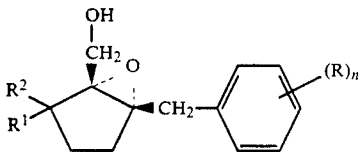 (IV)

in which n, R, $R^1$ and $R^2$ are as defined in claim 1, with a reducing agent at a temperature from 35° C. to reflux temperature; or
   (b) reacting a compound of the general formula

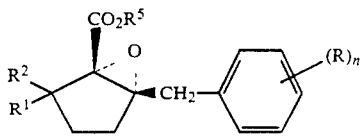 (V)

in which n, R, $R^1$, $R^2$ are as defined in claim 1 and $R^5$ represents a hydrogen atom or an alkyl or cycloalkyl group, with a reducing agent at a temperature form 35° C. to reflux temperature.

3. A process for the preparation of a compound of formula

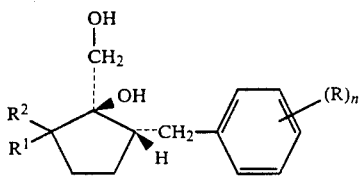 (IIB)

according to claim 1 which comprises reacting a compound of the general formula

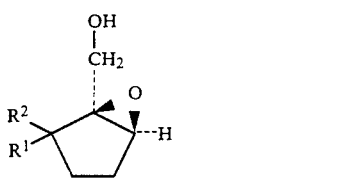 (XVII)

in which $R^1$ and $R^2$ are as defined in claim 1, with a compound of the general formula

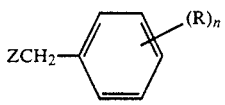 (XVIII)

in which n and R are as defined in claim 1 and Z represents a lithium atom or a group —MgX where X represents a halogen atom.

* * * * *

UNITED STATES PATENT AND TRADEMARK OFFICE
CERTIFICATE OF CORRECTION

PATENT NO.  : 5,075,513
DATED       : December 24, 1991
INVENTOR(S) : BRINER

It is certified that error appears in the above-identified patent and that said Letters Patent is hereby corrected as shown below:

On the cover page, in the Abstract, line 26 of the Abstract, "alkythio" should read --alkylthio--; and line 27 of the Abstract, "alkylamindo" should read --alkylamido--.

Signed and Sealed this

Eighteenth Day of May, 1993

Attest:

MICHAEL K. KIRK

Attesting Officer

Acting Commissioner of Patents and Trademarks

UNITED STATES PATENT AND TRADEMARK OFFICE
CERTIFICATE OF CORRECTION

PATENT NO. : 5,075,513
DATED : December 24, 1991
INVENTOR(S) : PAUL H. BRINER It is certified that error appears in the above-identified patent and that said Letters Patent is hereby corrected as shown below:

In claim 1, lines 9-14 of the claim, delete ", nitro, cyano, hydroxyl, alkyl, haloalkyl, alkoxy, haloalkoxy, amino, alkylamino, dialkylamino, alkoxycarbonyl, carboxyl, alkanoyl, alkylthio, alkylsulphinyl, alkylsulphonyl, carbamoyl, alkylamido, cycloalkyl or phenyl group".

Signed and Sealed this

Nineteenth Day of April, 1994

*Attest:*

BRUCE LEHMAN

*Attesting Officer*  *Commissioner of Patents and Trademarks*